(12) United States Patent
Millar et al.

(10) Patent No.: US 8,083,914 B2
(45) Date of Patent: Dec. 27, 2011

(54) ELECTROCHEMICAL GAS SENSOR

(75) Inventors: Andrew Peter Millar, Hampshire (GB); Martin Jonathan Kelly, Hampshire (GB)

(73) Assignee: Life Safety Distribution AG, Uster (CH)

( * ) Notice: Subject to any disclaimer, the term of this patent is extended or adjusted under 35 U.S.C. 154(b) by 215 days.

(21) Appl. No.: 11/971,620

(22) Filed: Jan. 9, 2008

(65) Prior Publication Data

US 2009/0057150 A1    Mar. 5, 2009

(30) Foreign Application Priority Data

Jan. 11, 2007 (GB) .................................. 0700556.4

(51) Int. Cl.
*G01N 27/413* (2006.01)
*G01N 27/407* (2006.01)
(52) U.S. Cl. ........ 204/432; 204/415; 204/431; 204/424; 73/23.31; 73/23.32; 73/31.02; 436/124
(58) Field of Classification Search .................. 204/406, 204/408, 412, 415, 421–435; 205/781, 783.5–785, 205/787; 73/23.31, 23.32, 31.02; 156/89.11–89.28; 436/124
See application file for complete search history.

(56) References Cited

U.S. PATENT DOCUMENTS

| | | | | |
|---|---|---|---|---|
| 4,370,206 A | * | 1/1983 | Razumney | 205/783 |
| 4,406,770 A | * | 9/1983 | Chan et al. | 204/406 |
| 4,446,000 A | | 5/1984 | Cullinane, Jr. | |
| 5,321,971 A | | 6/1994 | Hobbs et al. | |
| 5,331,310 A | | 7/1994 | Stetter et al. | |
| 5,344,546 A | * | 9/1994 | Kiesele et al. | 204/415 |
| 5,624,641 A | | 4/1997 | Capetanopolous et al. | |
| 5,827,948 A | * | 10/1998 | Martell et al. | 73/31.06 |
| 5,830,337 A | * | 11/1998 | Xu | 204/400 |
| 6,013,144 A | * | 1/2000 | Callaway | 149/108.2 |
| 6,099,293 A | * | 8/2000 | Kern et al. | 425/576 |
| 6,666,963 B1 | | 12/2003 | Peng et al. | |
| 2006/0196770 A1 | * | 9/2006 | Tomohiro et al. | 204/431 |

FOREIGN PATENT DOCUMENTS

| | | | |
|---|---|---|---|
| GB | 2 094 005 | | 9/1982 |
| GB | 2 094 005 A | | 9/1982 |
| WO | WO 2005/085824 | * | 9/2005 |

OTHER PUBLICATIONS

Per applicant's IDS submitted Jun. 11, 2008: "Liquid Electrolyte Fuel Cells", B.S. Hobbs, A.D.S. Tantram and R. Chan-Henry, Chapter 6 in "Techniques and Mechanisms in Gas Sensing", Eds. P.T. Moseley, J.O.W. Norris and D.E. Williams, Adam Hilger 1991.*
"Liquid Electrolyte Fuel Cells", B. S. Hobbs, A. D. S. Tantram and R. Chan-Henry, Chapter 6 in "Techniques and Mechanisms in Gas Sensing", Eds. P. T. Moseley, J. O. W. Norris and D. E. Williams, Adam Hiker 1991.
Communication; European Search Report; Mar. 10, 2010; pp. 1-7; Appln No. EP 08 10 0275; Place: Munich, Germany.

* cited by examiner

*Primary Examiner* — Jeffrey T Barton
*Assistant Examiner* — Jennifer Dieterle
(74) *Attorney, Agent, or Firm* — Husch Blackwell LLP

(57) ABSTRACT

An electrochemical gas sensor is disclosed which comprises a gas sensing electrode and a counter electrode disposed within a housing, the housing having an aperture for gas ingress, the gas sensing electrode and counter electrode being separated by a region containing electrolyte, and means for connecting the gas sensing electrode and the counter electrode to a sensing circuit. An electrolyte-absorbing element is disposed inboard of the aperture, between the housing and the gas sensing electrode, in order to absorb electrolyte passing through the gas sensing electrode whilst maintaining a gas path through the electrolyte-absorbing element.

30 Claims, 3 Drawing Sheets

ELECTROCHEMICAL GAS SENSOR

This invention relates to an electrochemical gas sensor having improved performance and longevity.

For the most part, the description hereinafter will focus on the example of an oxygen sensor. However, as detailed below, the principles of the invention are equally applicable to other types of electrochemical gas sensor, including oxygen pumps and toxic gas sensors.

Amperometric electrochemical oxygen sensors traditionally comprise a gas diffusion working electrode ("gas-sensing electrode"), often based on a graphite/platinum catalyst dispersed on PTFE tape. Oxygen is reduced at this cathode whilst a balancing oxidation takes place at a consumable anode ("counter-electrode"), most frequently made of lead (Pb). The electrodes are held within an outer housing which can retain a liquid electrolyte capable of supporting the relevant reactions, such as aqueous potassium acetate. A key feature of such sensor designs is the use of a controlled diffusion access which regulates the ingress of oxygen into the cell. By arranging that all oxygen is reacted at the cathode, the electrical output of the sensor may be directly related to the ambient oxygen concentration.

Such principles are well known and have been described for example in 'Liquid Electrolyte Fuel Cells', B S Hobbs, A D S Tantram and R Chan-Henry, Chapter 6 in 'Techniques And Mechanisms In Gas Sensing', Eds P T Moseley, J O W Norris and D E Williams, Adam Hilger 1991. However, there are many engineering challenges in ensuring that this approach can be translated into a rugged, reliable sensor for use in harsh environments. This is especially so given that users increasingly require longer life from such devices.

A conventional oxygen sensor construction is illustrated in FIG. 1. The outer housing (only the cap 10 is shown) is provided with a capillary gas inlet 12 which may typically be mechanically or laser drilled. A catalyst 14, for example a platinum/graphite/PTFE mixture, mounted on backing tape 16 (typically PTFE) together form the cathodic gas sensing or working electrode 20. This is thermally bonded or heat staked to the sensor cap 10, usually around a circumferential zone 22 outside of the catalyst footprint, although bonding directly over the catalyst is also possible. A gas diffusion member 30 in the form of a (preferably flexible) disc bonded to a mesh 31 is trapped between the electrode assembly 20 and the cap 10. Its purpose and operation are discussed further below.

The gas sensing electrode 20 is separated from a counter-electrode 56 by separators (for example 41,42) which, when saturated with electrolyte, wet up the active surface and provide an electrolytic pathway through region 40 between the two electrodes 20,56. In addition, they cushion the flexible structure against the counter-electrode 56 which might otherwise cause damage. A current collector 50 runs from the gas sensing electrode to one external connection, whilst a basket 54 (typically made of nickel) is typically used to act as a means of ensuring reliable contact to the counter electrode 56 and is linked to a second external pin by current collector 58. The external pins connect the electrodes to a sensing circuit in use.

The entire assembly is charged with electrolyte, which wets up the active surfaces of the electrodes 20,56, and then sealed, typically by ultrasonically welding the cap 10 to the base of the sensor housing (not shown). This action also places the entire structure under a significant degree of compression. This is necessary to ensure that a good contact is maintained between separators 41,42 and catalyst 14 on the gas-sensing electrode 20. If this contact is inadequate, then the output signal is prone to fluctuations which are naturally undesirable.

Such designs and assembly techniques have been used in a number of commercial products over some years. However, there are a number of issues relating to the performance and interaction of the electrolyte, electrode backing tape 16 and the diffuser 30 which still cause operational difficulties and it is with these matters that the present invention is particularly concerned.

The diffuser element 30 is employed in order to prevent a phenomenon known as 'plugging'. This occurs when gas entering the sensor through the capillary 12 impinges directly on to the electrode backing tape 16. The properties of the tape 16 are chosen largely on the basis of providing a good hydrophobic support for the catalyst mixture as well as a high degree of gas diffusibility. However, even relatively porous tapes do present a degree of diffusion resistance to incoming gas, with the result that the rate of gas arrival at the active electrode surface is not solely controlled by the properties of the capillary 12. In effect, a 'plug' of gas located in a small zone under the capillary 12 builds up as a result of electrode control. A secondary impact is that the electrode utilisation may not be equally effective across a majority of the surface resulting in poorer efficiency.

The existence of any degree of tape control within the sensor is undesirable. The cell design relies on known, controlled (and stable) properties of the capillary in order to deliver the required performance. The output sensitivity, lifetime (in this example the lead anode is consumed by its oxidation reaction), pressure and temperature characteristics of the device are all controlled to a large extent by the properties of this aperture. However, the degree of electrode control is variable, depending upon the precise mechanical condition of the tape and the stresses within it, and may vary with age, as discussed below. Thus, a reliable and stable cell design must incorporate measures to prevent the precise condition of the tape exerting a significant impact on the performance by ensuring that it has adequate diffusibility to cope with the gas flux to which it is exposed under all intended working conditions throughout the life of the sensor.

The tape 16 not only affects key gas diffusion parameters in the sensor whilst supporting the electrocatalyst and maximising the interfaces between catalyst, gas and electrolyte at which the key electrochemical processes occur. It is also, crucially, required to act as a hydrophobic barrier, preventing the electrolyte (which may be an aggressive alkali such as 4-molar potassium acetate) from leaking out of the cell. Apart from the obvious health and safety implications, such leakage will inevitably damage the sensor and shorten its life.

Given the importance of the backing tape performance, it is necessary to pay due attention to aspects of the design and assembly process which may affect its condition. For example—

(i) The electrode assembly is typically fabricated by pressing a layer of catalyst onto the backing tape. This in itself can result in stress concentrations in the tape which can develop into areas of weakness.

(ii) As the electrode backing tape is heat staked to the underside of the sensor top, it tends to be radially stretched. This puts the fabric of the tape under stress and can open up or emphasise any minor imperfections which inevitably exist within such materials.

(iii) In the given example, a consequence of the lead oxidation anode reaction is an increase in volume. This causes increased stress within the (already compressed) structure and can also increase the severity of minor flaws as the lead bulk presses up into the electrode stack. Such changes may occur over many months or years.

Thus, the backing tape may be damaged (or have inherent weaknesses exposed) either during the assembly process or as a consequence of changes which naturally occur during the normal operating life of the sensor. Whilst some gross defects may be detected by testing immediately after sensor assembly, others are more difficult to detect.

One major impact of microscopic flaws or holes in the tape is a phenomenon known as 'sweating'. This occurs when electrolyte permeates or is forced through small openings in the tape and forms droplets on the capillary side of the tape Such droplets may detrimentally affect the diffusion characteristics of the sensor, and if the electrolyte dries out, solid crystals may form and obstruct the capillary access. In either case, a fall in the output of the device may result, which can cause operational problems.

Given that is difficult to ensure 100% integrity of such tapes, and the necessity of addressing the 'plugging' issue, gas diffusers, located in the same position as element 30 shown in FIG. 1, were introduced into such sensor designs. Initially, fibrous material of the same type as that used for separators (such as 40,42) was employed, as it was found to offer appropriate gas diffusion characteristics. An example of such material is Viledon FS2145WI (Freudenberg Nonwovens L.P, UK), a polyamide nonwoven separator—other examples may employ glass wool. Materials of this type are used where it is desirable to maintain wetting under a wide range of conditions—for example where one seeks to bring a solid catalyst into contact with a liquid electrolyte as is frequently required in batteries or fuel cells. Their inorganic fibrous components are generally not designed to absorb the liquid to which they are exposed. Rather, they are intended to maintain it in a liquid state within narrow pores which exist within the 3 dimensional structure formed by the interlinked fibres. Indeed, the strong capillary action which can exist in such circumstances is the primary reason why such materials are favoured choices for wicks within electrochemical sensors when it is necessary to transport liquid electrolyte from one location to another.

However, these essentially hydrophilic components exhibit such strong attraction for electrolyte which enters the key region between the capillary and the PTFE backing tape, that their pores become saturated and under such conditions, offer poor gas diffusibility, causing operational problems. Crystallisation of electrolyte in and around this component was also observed under a wide range of scenarios which contributed to poor overall performance of the sensor.

Recognising these problems, a further development involved the replacement of the hydrophilic diffuser with a hydrophobic component. This took the form of a woven open mesh containing highly permeable PTFE membrane bonded to a polypropylene scrim, as shown in FIG. 1. This offers a partial solution by offering an additional hydrophobic barrier to prevent electrolyte residing in the area immediately under the capillary. But in severe cases, even this can be overwhelmed and allow some degradation in output signal. In addition, the open weave of the mesh concentrates pressure into relatively small areas of the electrode tape as the sensor is assembled and compressed, which may actually exacerbate the sweating problem.

A more effective solution to these significant problems is therefore required.

In accordance with the present invention, an electrochemical gas sensor comprises a gas sensing electrode and a counter electrode disposed within a housing, the housing having an aperture for gas ingress, the gas sensing electrode and counter electrode being separated by a region containing electrolyte, and means for connecting the gas sensing electrode and the counter electrode to a sensing circuit, wherein an electrolyte-absorbing element is disposed inboard of the aperture, between the housing and the gas sensing electrode, in order to absorb electrolyte passing through the gas sensing electrode whilst maintaining a gas path through the electrolyte-absorbing element.

By incorporating an electrolyte absorbing element into the assembly stack, any electrolyte passing through the electrode is absorbed and so allowed to dry out without any detrimental effects on cell performance. By "absorbing" the electrolyte, it is meant that the material making up the electrolyte-absorbing element is able to absorb the electrolyte. This is fundamentally different to the behaviour of materials such as PTFE tape, which is hydrophobic, or separator material (described above) which does not absorb liquid but rather traps it within its structure. In the electrolyte-absorbing element of the present invention, on the other hand, the material itself is able to absorb liquid electrolyte to which it is exposed. For precisely this reason, such materials are not used as wicks or separators since little free liquid is available within them.

Preferably, the electrolyte-absorbing element is adapted to absorb electrolyte in a manner which does not significantly impede the passage of gas therethrough. That is, the element does not exhibit any tendency to allow liquid to crystallise or otherwise solidify within its structure, to saturate gas passages such as pores therein, or cause major swelling of the material which could otherwise constrict such gas passages.

In a preferred embodiment, the electrolyte-absorbing element comprises one or more bodies of electrolyte absorbent material, which are capable of absorbing electrolyte such that it is contained within the bodies. In other words, the electrolyte is retained within the material itself and not simply held in pores or other cavities, where it could cause obstruction.

Advantageously, the one or more bodies of electrolyte absorbing material are adapted to undergo substantially no increase in volume on absorption of electrolyte. That is, the absorption occurs without significant swelling which could otherwise lead to blocking of pores between the bodies, so that the material retains an acceptable degree of gas diffusibility. Thus, up to the saturation limit of the material, the absorbing element helps to prevent crystallisation of the electrolyte in the critical area whilst maintaining its gas diffusion action.

In a particularly preferred embodiment, the bodies are one or more of fibres, flakes or particles of electrolyte adsorbent material. For example, the electrolyte-absorbing element advantageously comprises an arrangement of interleaved fibres defining gaps or pores therebetween.

Advantageously, the electrolyte-absorbing element is porous or cellular, the pores or cells preferably being interconnected to allow the passage of gas therethrough. The pores or cells could be defined by numerous separate bodies as previously described, or by a continuous structure such as foam or sponge.

Preferably, the electrolyte absorbing element comprises a cellulose-based, electrolyte absorbent material. This type of material has been found to be particularly well suited to this application, especially where an alkaline electrolyte is employed.

In a particularly preferred embodiment, the electrolyte-absorbing element comprises filter paper. This is a readily available form of suitable material, and is straightforwardly incorporated into the manufacturing process.

The electrolyte-absorbing element may be employed alone, fulfilling the function of the gas diffusion member previously described. However, it is preferable that the electrochemical gas sensor further comprises a gas diffusion member disposed adjacent to the electrolyte-absorbing element, between the housing and the gas sensing electrode. The use of the absorbing element in addition to (and preferably concentric with) a gas diffusion member as used in conventional sensors, provides a secondary benefit in that the absorbing element cushions the gas diffusion element against the electrode backing tape and reduces the risk of damage arising from high compression within the sensor.

Preferably, the gas diffusion member comprises a PTFE membrane. Advantageously, the gas diffusion member is supported by a mesh. Preferably, the mesh comprises a scrim, preferably a polypropylene scrim. Here, the term "scrim" is used to indicate a layer of loosely woven, open mesh material. As well as supporting the gas diffusion member, the scrim helps to prevent electrolyte entering the gas diffusion member from where it could leak into the capillary region. Preferably, the mesh is intimately bonded to the gas diffusion member.

In a preferred example, the region containing electrolyte comprises one or more separators adapted to hold electrolyte therewithin and supply electrolyte to the gas sensing electrode and the counter-electrode. In certain embodiments, it is advantageous that the electrochemical gas sensor further comprises a reservoir containing electrolyte in use, and a wick for conveying electrolyte from the reservoir to the region containing electrolyte. This is of particular use in toxic gas sensors. In oxygen sensors, any electrolyte not held within the separators can be contained in the same region as the lead anode.

Preferably, the gas sensing electrode comprises a catalyst disposed on a backing tape. The catalyst preferably comprises graphite and/or platinum. The backing tape preferably comprises PTFE.

In a particularly preferred embodiment, the counter-electrode comprises a consumable electrode. Advantageously, the consumable electrode comprises lead, zinc, copper or iron.

In alternative embodiments, the counter-electrode may comprise a catalyst disposed on a backing tape, in a similar manner to the gas sensing electrode.

Depending on the type of cell, the sensor may operate in a two electrode mode, with a combined counter reference electrode, or a three electrode mode. In a three electrode mode, the gas sensor further comprises a reference electrode.

Advantageously, the aperture for gas ingress comprises a capillary. Other types of well-known diffusion barriers, such as solid polymer (e.g. non-porous PTFE) barriers could be used instead.

Preferably, at least the gas sensing electrode is heat sealed within the housing. Additional components such as the electrolyte-absorbing element and/or the gas diffusion element may be held in position by trapping them between the electrode and the housing. The electrolyte-absorbing element may advantageously be fixed relative to the housing adhesive or adhesive tape, in addition or as an alternative. The gas diffusion element may be similarly affixed to the housing.

Preferably, the electrochemical gas sensor is adapted for the detection of oxygen, although the principles of the present invention are equally applicable to the sensing of other gas species.

An example of an electrochemical gas sensor in accordance with the present invention will now be described and contrasted with a known sensor with reference to the accompanying drawings, in which;—

The present invention finds application in any electrochemical gas sensor wherein a supply of gas to one or more of the electrodes might be impeded by misplaced electrolyte. As already indicated, oxygen sensors tend to be particularly prone to phenomena such as "plugging" and "sweating". Sweating is due in particular to the stresses experienced by the electrode backing tape during heat staking and expansion of the consumable electrode during use. However, such problems are not exclusive to this type of sensor but may also be encountered by toxic gas sensors and oxygen pumps, amongst others.

In general, there have been far fewer problems involving electrolyte sweating through electrode tape in toxic sensor designs, although the PTFE tapes and catalyst pressing methods are largely common. However, toxic cells have much lower compression applied during sealing (due to the different counter electrode type usually employed), and this is believed to be a key factor. Even if electrolyte sweating did occur, its impact might be greatly reduced over that seen in oxygen sensors by the much larger capillary diameters usually employed. Additionally, the electrolyte normally used in toxic cells (5M sulphuric acid) is not as prone to crystallisation as that used in oxygen sensors (potassium acetate).

That said, any sensor that uses a catalyst/backing tape electrode configuration and intends the backing tape to act as an electrolyte barrier is prone to "sweating", since the very process of pressing the catalyst onto the PTFE tape tends to cause stresses in the tape which can allow leakage of electrolyte therethrough. Nonetheless, the present description will focus on the example of an oxygen sensor but it will be appreciated that the scope of the invention is not so limited.

Figure 1:
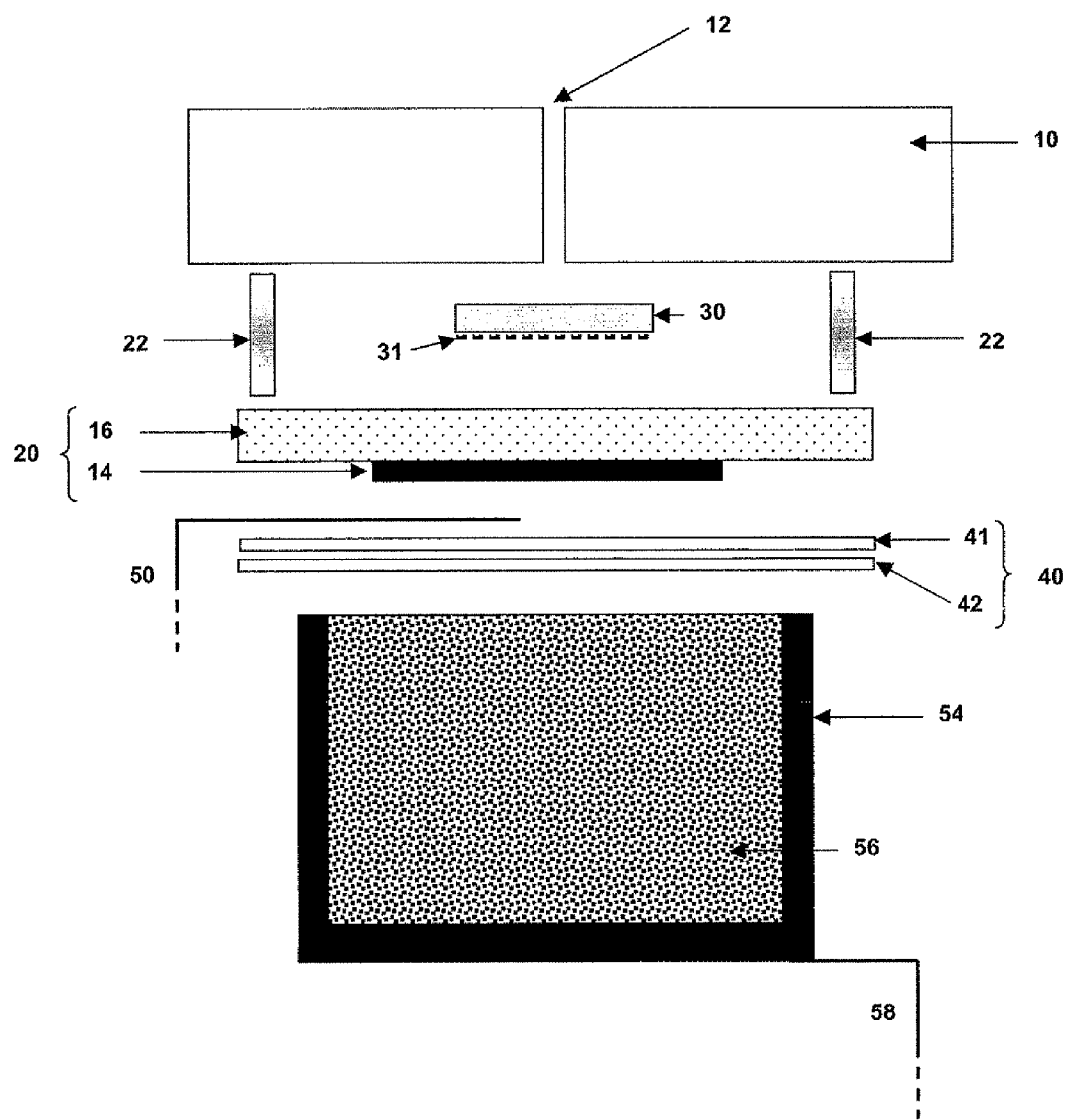
FIG. 1 is a schematic cross-section of an electrochemical gas sensor which operates according to known principles.
Figure 2:
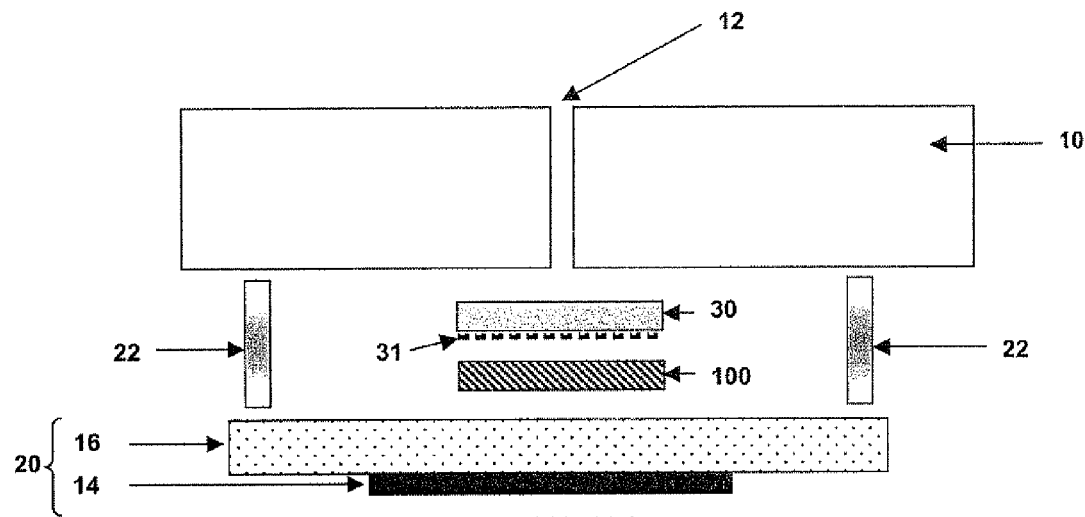
FIG. 2 is a schematic cross-section of a first embodiment of an electrochemical gas sensors in accordance with the present invention, showing only selected components.

The configuration of a conventional oxygen sensor has already been described with respect to FIG. 1 above. FIG. 2 shows the main components of a gas sensor in accordance with the first embodiment of the present invention using the same reference numerals as FIG. 1 for like components. Those components which are not relevant to the present discussion have been omitted from the drawing for clarity. Thus, the Figure does not depict the electrolyte containing region nor the counter-electrode which would typically be provided underneath the gas sensing electrode 20. In the case of an oxygen sensor, these components will be identical to those shown in FIG. 1. For contrast, were the principles of the invention to be employed in a toxic gas sensor, for example, the counter-electrode might be provided in the form of a second catalyst/backing tape assembly, along with a electrolyte reservoir and wick arrangement for supplying the separators with electrolyte (not shown). Details of a typical toxic gas sensor arrangement can be found in GB2094005.

Regardless of the electrode configuration selected, there will be an electrolyte containing region (e.g. 40 in FIG. 1) immediately below the gas sensing electrode 20, which is made up of catalyst 14 and backing tape 16. Between the gas sensing electrode 20 and the cap 10 of the housing, an electrolyte-absorbing element 100 is disposed. The electrolyte-absorbing element 100 is capable of absorbing electrolyte which passes through the backing tape 16, in a manner which does not significantly impede progress of gas through the element 100. That is, the element 100 absorbs electrolyte into the material itself, rather than merely holding it in pores or other cells within the element's structure. In this way, the electrolyte is dried out without risk of crystallisation or saturation which would lead to obstructions. Further, the electrolyte absorbent material is preferably chosen such that there is minimal swelling of the material making up element 100 in order that the channels which allow for the flow of gas therethrough are not constricted significantly. In most cases, it is envisaged that the electrolyte absorbing element 100 has no activity with respect to the passing gas stream (i.e. it is inert).

In the present example, the electrolyte-absorbing element 100 is cellulose-based and comprises an arrangement of interleaved fibres defining pores therebetween. For example, filter paper has been found to have the required properties. Other grades of cellulose-based papers are also expected to exhibit these characteristics, e.g. blotting paper would be a suitable substitute.

In this example, the electrolyte-absorbing element 100 is provided in the form of a disc having a reduced diameter compared to the catalyst 14 and PTFE backing tape 16. However, in other examples, it may be advantageous for the electrolyte absorbing element 100 to extend across the whole diameter of the cell. The element may be of any convenient shape and dimensions. What is of importance is that the element 100 is provided in the area under capillary 12 to ensure that gas flow is unrestricted in this region.

Optionally, a gas diffusion element 30, as used in conventional oxygen sensors, may be provided adjacent to the electrolyte absorbing element 100. As in conventional designs, the gas diffusion element 30 is preferably provided in the form of a disc of hydrophobic material such as PTFE. The membrane is typically bonded to a polypropylene scrim for support and to prevent ingress of electrolyte into the PTFE material from where it might otherwise leak into the capillary region. The scrim is a loosely woven open mesh which acts as an additional electrolyte barrier.

It is believed that the scrim operates in this way due to the droplets of electrolyte initially forming concentrations local to the weave of the scrim. Only once the amount of "sweating" increases past a certain threshold, do the droplets "spill over" from the weave onto the surface of the gas diffusion element, from where they can leak into the capillary region.

The gas diffusion element 30 is cushioned against the electrode backing tape 16 by the electrolyte absorbing element, thereby reducing the risk of damage arising from high compression within the sensor.

Figure 3:
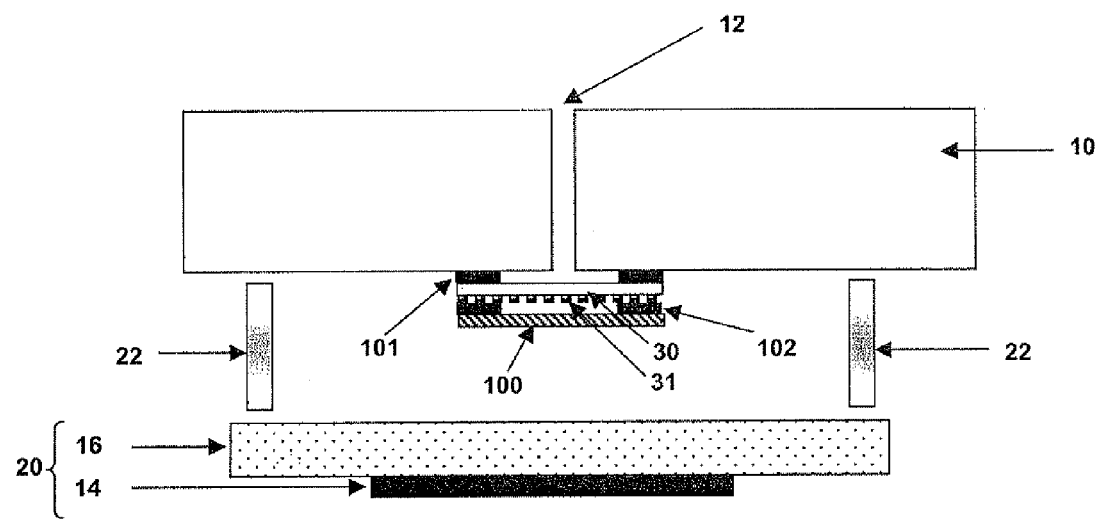
FIG. 3 is a schematic cross-section of the first embodiment showing additional components used to demonstrate the structure of the gas sensor in use.

FIG. 3 is the same view as that depicted in FIG. 2, but now the gas diffusion elements 30 and electrolyte-absorbing element 100 are shown with additional components to hold the elements in assembled relation to one another. The thicknesses of the two elements 30,100 are also shown at a reduced scale compared to FIG. 2, in order to demonstrate how, in this example, they are mounted to cap 10 of the housing. The gas diffusion element 30 is affixed to the interior of the cap 10 via a first adhesive 101, applied along an annular path around the periphery of gas diffusion element 30. The adhesive 101 may be provided in the form of a glue or as an adhesive tape. A second adhesive 102 is used to support the electrolyte absorbing element 100 on the underside of the gas diffusion element 30. The second adhesive 102 is typically provided in the form of an adhesive tape or glue having an annular shape.

The adhesives 101 and 102 are primarily provided in order to locate the elements 30 and 100 in the desired position centred on capillary 12. The main force acting on the components 30 and 100 is provided by heat sealing the electrode 20 to the underside of cap 10 around circumferential region 22. This applies compression to the gas diffusion element 30 and electrolyte absorbing element 100 and retains them in position. However, the use of adhesives 101 and 102 is advantageous since it prevents any lateral slippage during assembly or during the life of the sensor. During assembly, the cap, the electrolyte absorbing element and the gas diffusion element can be affixed to one another and the unit handled as a sub-assembly during further processing.

Alternatively, the electrolyte absorbing element 100 can be directly heat-staked to cap 10, sandwiching the gas diffusion element 30 therebetween. In this case, the electrolyte absorbing element 100 would preferably have a diameter greater than that of the gas diffusion element 30 but less than that of the electrolyte backing tape 16. The adhesives 101 and 102 could be eliminated or used in addition.

Figure 4:
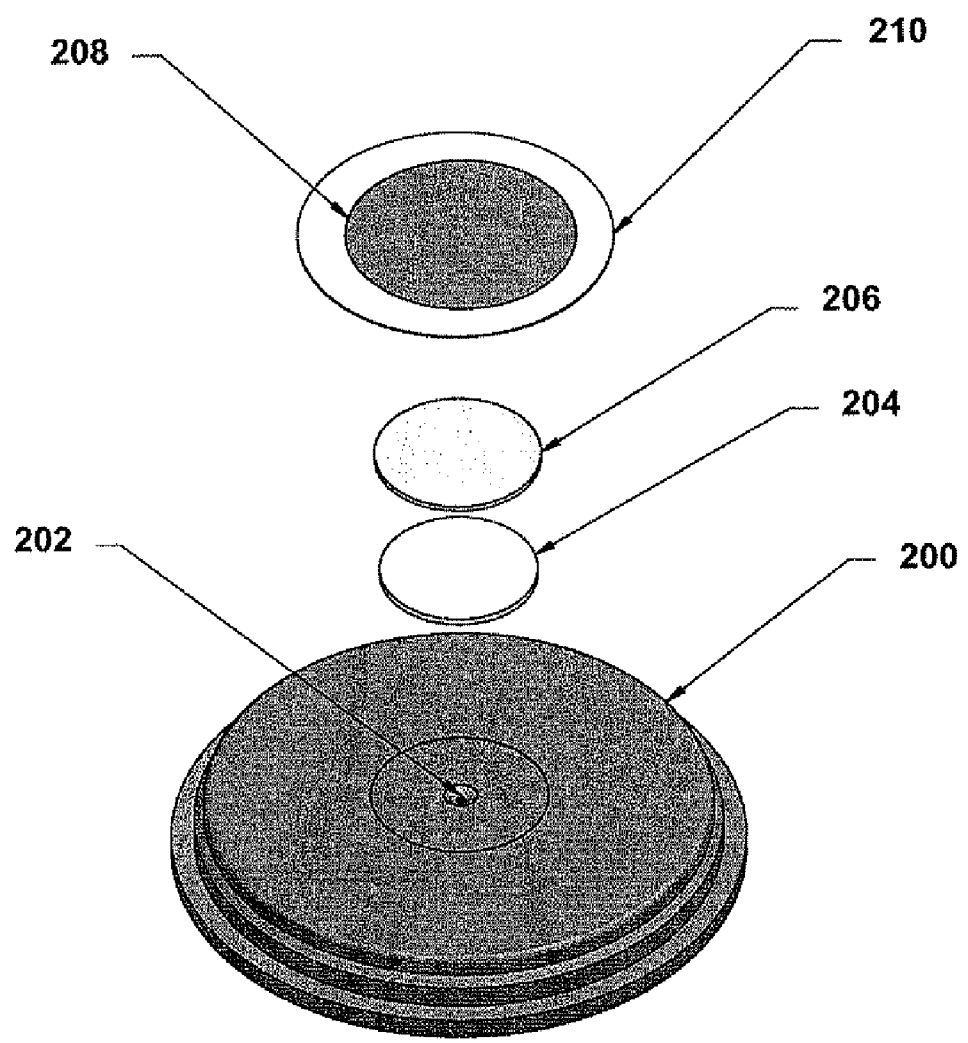
FIG. 4 is an exploded view of a second embodiment of a gas sensor according to the present invention, showing only selected components.

FIG. 4 is an exploded view showing the relevant components of a second embodiment of the invention. Again, the remainder of the cell components, including the counter-electrode and electrolyte arrangements have been omitted for clarity. The arrangement shown is based on the 4OX-2 oxygen sensor produced by City Technology Limited. An ABS plastic cap 200, provided with a laser drilled capillary hole 202, having a typical diameter of approximately 60 microns, is concentrically arranged with a 5.9 millimetre diameter mesh gas diffusion element 204 (type L32224 provided by W L Gore and Associates, USA) and a 6 millimetre electrolyte-absorbing element 206 punched from grade 4 qualitative filter paper provided by Whatman International Limited of Maidstone, United Kingdom. A gas sensing electrode, comprising a 9 millimetre diameter 5% platinum on graphite catalyst 208 on an 11 millimetre diameter PTFE disc 210 (type HP5815934, provided by W L Gore and Associates, USA) is then heat sealed onto the cap 200 to produce a sub-assembly employed in the remainder of the sensor manufacturing process.

The effectiveness of this arrangement in absorbing electrolyte and allowing it to dry out without detrimental impact on the sensor performance has been demonstrated by a severe test. Before assembly of the sensor, the absorber element 206 was dosed with a volume of 4-molar potassium acetate electrolyte typically found to pass through the electrode tape in occurrences of "sweating". This "stimulated sweating" is a good approximation of the actual conditions to be experienced by the element in situ. The completed device was then run through a temperature test involving ramping from −20 to +50C in 4 hours and then reversing the sweep at the same rate. This was continued for a total of 72 hours during which normal stable outputs were observed. At the end of this period the sensor was dismantled and on inspection the electrolyte absorbing element 206 was found to be dry, with no sign of electrolyte crystallisation. Similar test regimes have been shown to be efficient at highlighting potential design weaknesses in oxygen sensors and it is therefore believed that the new design represents a robust and effective solution to this significant operational problem. Further, the additional cost of the absorber is minimal and the sensor assembly process is not significantly affected by its inclusion.

We claim:
1. An electrochemical gas sensor comprising:
  a housing, the housing defining a gas inlet therethrough and also an interior surface; and
  a stacked combination of an electrolyte absorbing material, adjacent to the surface and an overlying gas sensing electrode that detects oxygen with one entire side of the electrolyte absorbing element directly facing the overlying gas sensing electrode, a peripheral region of the gas sensing electrode positioned adjacent to and in con- tact with a portion of the surface, the gas sensing electrode covering an end of the gas inlet, with the electrode being bonded to an annular region of the surface, around the inlet, the absorbing material is retained between the surface and a portion of the electrode, by an annular bond, forming a unitary multi-layered subassembly wherein the electrolyte absorbing material absorbs on the facing side any liquid electrolyte passing through the gas sensing electrolyte to prevent any detrimental effects on cell performance caused by liquid electrolyte residing in the region of the gas inlet.

2. A gas sensor as in claim 1 where the combination includes a gas diffusion element positioned between the surface and the electrolyte absorbing material.

3. A gas sensor as in claim 1 where being bonded comprises at least one of a heat sealed bond, or, an adhesive bond.

4. An electrochemical gas sensor comprising
a gas sensing electrode and a counter electrode that detect oxygen disposed within a housing,
the housing having a surface with an aperture for gas ingress,
the gas sensing electrode and counter electrode being separated by a reservoir containing electrolyte, the reservoir providing an electrolytic pathway between the gas sensing electrode and the counter electrode,
collectors for connecting the gas sensing electrode and the counter electrode to a sensing circuit, and
an electrolyte-absorbing element disposed inboard of the aperture, between the aperture in the surface of the housing and the gas sensing electrode with one entire side of the electrolyte-absorbing element directly facing the gas sensing electrode, wherein the electrolyte-absorbing element absorbs any liquid electrolyte passing through the gas sensing electrode from the reservoir containing electrolyte to prevent any detrimental effects on cell performance caused by liquid electrolyte residing in the region of the aperture whilst being inert to gas passing through the electrolyte-absorbing element and wherein the gas sensing electrode is at least in part bonded to the surface and the electrolyte-absorbing element is captured between the surface of the housing and at least a portion of the gas sensing electrode.

5. An electrochemical gas sensor according to claim 4, wherein the electrolyte-absorbing element absorbs electrolyte in a mariner which does not significantly impede the passage of gas therethrough.

6. An electrochemical gas sensor according to claim 4 wherein the electrolyte-absorbing element is porous or cellular, the pores or cells preferably being interconnected to allow the passage of gas therethrough.

7. An electrochemical gas sensor according to claim 4 wherein the electrolyte-absorbing element comprises a cellulose-based, electrolyte-absorbent material.

8. An electrochemical gas sensor according to claim 4 wherein the electrolyte-absorbing element comprises filter paper.

9. An electrochemical gas sensor according to claim 4 wherein the reservoir containing electrolyte comprises one or more separators adapted to hold electrolyte therewithin and supply electrolyte to the gas sensing electrode and the counter electrode.

10. An electrochemical gas sensor according to claim 4 wherein the counter electrode comprises a catalyst dispersed on a backing tape.

11. An electrochemical gas sensor according to claim 4 further comprising a reference electrode.

12. An electrochemical gas sensor according to claim 4 wherein the aperture for gas ingress comprises a capillary.

13. An electrochemical gas sensor according to claim 4 wherein at least the gas sensing electrode is heat-sealed to the surface of the housing.

14. An electrochemical gas sensor according to claim 4 wherein the electrolyte-absorbing element is fixed relative to the housing via adhesive or adhesive tape.

15. An electrochemeical gas sensor as in claim 4 where the electrode is bonded to the surface by at least one of a heat sealed bond, or an adhesive bond.

16. An electrochemical gas sensor according to claim 4 wherein the counter electrode comprises a consumable electrode.

17. An electrochemical gas sensor according to claim 16 wherein the consumable electrode comprises lead (Pb), zinc (Zn), copper (Cu) or iron (Fe).

18. An electrochemical gas sensor according to claim 4 wherein the gas sensing electrode comprises a catalyst dispersed on a backing tape.

19. An electrochemical gas sensor according to claim 18 wherein the catalyst comprises graphite and/or platinum.

20. An electrochemical gas sensor according to claim 18 wherein the backing tape comprises PTFE.

21. An electrochemical gas sensor according to claim 4, wherein the electrolyte-absorbing element comprises one or more bodies of electrolyte-absorbent material, which absorb electrolyte such that it is contained within the bodies.

22. An electrochemical gas sensor according to claim 21 wherein the bodies are one or more of fibres, flakes or particles of electrolyte-absorbent material.

23. An electrochemical gas sensor according to claim 22, wherein the one or more bodies of electrolyte-absorbing material undergo substantially no increase in volume on absorption of electrolyte.

24. An electrochemical gas sensor according to claim 23 wherein the bodies are one or more of fibres, flakes or particles of electrolyte-absorbent material.

25. An electrochemical gas sensor according to claim 4 further comprising a gas diffusion member disposed adjacent to the electrolyte-absorbing element, between the housing and the gas sensing electrode.

26. An electrochemical gas sensor according to claim 25 wherein the gas diffusion member is hydrophobic.

27. An electrochemical gas sensor according to claim 25 wherein the gas diffusion member comprises a PTFE membrane.

28. An electrochemical gas sensor according to claim 25 wherein the gas diffusion member is supported by a mesh.

29. An electrochemical gas sensor according to claim 28 wherein the mesh comprises a scrim, preferably a polypropylene scrim.

30. An electrochemical gas sensor according to claim 28 where in the mesh is intimately bonded to the gas diffusion member.

* * * * *